United States Patent [19]

Obersat

[11] Patent Number: 5,194,002

[45] Date of Patent: Mar. 16, 1993

[54] ANCHOR FOR SECURING A DETACHABLE PART TO A FIXEDLY MOUNTED PART OF A DENTAL PROSTHESIS

[76] Inventor: Adam Obersat, Logenstrasse 4, D-6750 Kaiserslautern, Fed. Rep. of Germany

[21] Appl. No.: 561,311

[22] Filed: Aug. 1, 1990

[30] Foreign Application Priority Data

Aug. 1, 1989 [DE] Fed. Rep. of Germany ... 8909278[U]
Oct. 31, 1989 [DE] Fed. Rep. of Germany ... 8912852[U]

[51] Int. Cl.$^5$ ..................... A61C 13/12; A61C 13/225
[52] U.S. Cl. .................................................. 433/182
[58] Field of Search ............... 433/172, 181, 182, 183, 433/177

[56] References Cited

U.S. PATENT DOCUMENTS

| | | | |
|---|---|---|---|
| 4,196,516 | 4/1980 | Poveromo | 433/182 |
| 4,380,436 | 4/1983 | Kipp | 433/182 |
| 4,474,499 | 10/1984 | Pedrazzini | 433/181 |
| 4,746,295 | 5/1988 | Kipp | 433/183 X |
| 4,773,859 | 9/1988 | Obersat | 433/181 X |
| 4,790,754 | 12/1988 | Weissman | 433/181 X |
| 4,973,249 | 11/1990 | Silvio et al. | 433/181 X |
| 5,040,985 | 8/1991 | Obersat | 433/181 |

Primary Examiner—Gene Mancene
Assistant Examiner—Nicholas D. Lucchesi
Attorney, Agent, or Firm—Peter K. Kontler

[57] ABSTRACT

An anchor for securing a detachable part to a fixedly mounted part of a dental prosthesis consists of a patrix which has an undercut portion and a second coupling member (12) which surrounds the first coupling member in ring-like fashion and extends into the undercut portion with at least one resilient detent element (14,20). The detent element (17,20) extends tangentially of the patrix and is held in a flat recess (41) of the second coupling member (12;112) at both sides of the location where it extends into the undercut portion of the patrix. It is preferred to provide two detent elements (17, 20) on a U-shaped insert member which can be pushed into and withdrawn from a complementary recess (16) of the second coupling member (12;112) with releasable locking action. The insert member can simply constitute a bendable spring, and the detent elements (17, 20) are constituted by a U-shaped leg (17).

13 Claims, 3 Drawing Sheets

ANCHOR FOR SECURING A DETACHABLE PART TO A FIXEDLY MOUNTED PART OF A DENTAL PROSTHESIS

BACKGROUND OF THE INVENTION

The invention relates to an anchor for securing a detachable part to a fixedly mounted part of a dental prosthesis, the anchor consisting of a first coupling member which is provided with an undercut portion and a second coupling member which annularly surrounds the first coupling member and has at least one resilient detent element which extends into the undercut portion.

Such an anchor is known and is in actual use. The resilient detent element consists of a resilient ring which is disposed in a ring-shaped groove of the second coupling member. The ring is expanded during insertion of the first coupling member to be pushed back into the ring-shaped groove in its entirety and to extend in part into the ring-shaped groove and in part into the undercut portion when the inserting step is completed.

OBJECT OF THE INVENTION

The object underlying the invention is to provide an anchor of the afore described type with a detent element which can generate sufficient retaining force and renders it possible to more accurately select the separating force.

SUMMARY OF THE INVENTION

In accordance with the invention, this purpose is accomplished in that the detent element extends tangentially of the first coupling member and is held in a flat recess of the second coupling member at both sides of the location where it extends into the undercut portion of the first coupling member.

This renders it possible to achieve extremely small dimensions, especially in the height of the anchor, as well as long useful life.

In accordance with an advantageous embodiment of the invention, the detent element or the detent elements—as a rule, two detent elements are provided opposite each other—is or are provided on a U-shaped insert member which can be pushed into and withdrawn from a complementary recess of the second coupling member, preferably with releasable locking action, the U-web being accommodated in a slot which is open toward the periphery of the second coupling member. Furthermore, this enables a dentist to rapidly exchange a worn detent element in a simple manner at the dentist's chair; the detent element can be engaged at its U-web. The first insertion is equally simple.

On the other hand, the conventional resilient ring is so difficult to remove from the ring-shaped groove that the second coupling member was already divided and held together at the ring-shaped groove by a screw.

In accordance with an especially simple and advantageous modification, the insert member is a bendable spring and the detent element is or the detent elements are formed by a U-shaped leg of the bendable spring, the leg being preferably provided with a roller.

In accordance with another modification, the insert member is a resilient holder for the detent element resp. for the detent elements which detent element or elements consists or consist of a roller mounted on a springy or non-resilient shaft.

This modification renders it possible to completely or partially separate the function of the spring from the locking function of the detent elements and the bearing function of the shafts and to transfer the function of the spring into the holder for which one can select a more elastic material and/or which can constitute an additional spring with a softer spring action. Furthermore, the insert member which can constitute a holder for the shaft(s) and roller(s) can have a U-shaped inwardly open cross section to close the recess in the second coupling member in drawer-like fashion and to thus prevent penetration of remnants of food.

A particular advantage of detent elements which, in accordance with the invention, extend tangentially of the first coupling member is the possibility to equip such detent elements with the aforementioned rollers. The rollers greatly reduce friction and thus render it possible to rather accurately adjust the separating force, namely the force which is required to detach the detachable prosthesis from the fixedly mounted part of the prosthesis by overcoming the blocking action of the detent element, only in dependency upon the characteristic curve of the springy part of the detent element on the one hand and upon the configuration of the undercut portion on the other hand. In other words, the inclination of the undercut portion can be selected at an angle such that, in combination with the characteristic curve of the spring, the first coupling member can be extracted from the second coupling member with a predetermined force by pushing back the detent element or detent elements.

The roller or the rollers preferably have a cylindrical or concave periphery preferably conforming to the deepmost portion of the undercut portion of the first coupling member.

The concave periphery corresponds to the normally circular cross section of the first coupling member and the inner cross section of the second coupling member. The preferably elongated cylindrical periphery lies satisfactorily tangentially against the first coupling member and would be possible even in the case of a rectangular cross section. In addition, it is simple to produce. For example, it is merely necessary to sever a piece from a small tube which was produced for other purposes.

The U-shaped legs of the holder—of the actual bendable spring as well as of the resilient holder—can be curved slightly inward to ensure that they by themselves act as a bendable spring during assembly of the first coupling member and second coupling member in such a way that their curved portion is pushed back and flattened.

A roller which is mounted directly on the bendable spring requires a correspondingly large inner diameter. However, when considered from another point of view, the roller has a straight shaft and an inner diameter which conforms thereto.

As a rule, the U-shaped bendable spring will be equipped with two rollers. However, it is also considered to employ a single roller, namely in order to take advantage of full deflection of the spring. This corresponds substantially to a halving of the slope of the characteristic curve.

The U-shaped legs of the bendable spring are preferably bent inwardly close to both ends to be anchored in the second coupling member by engaging behind a narrowed portion which is provided in the second coupling member.

The ends of the bendable spring can be held in a suitable manner against yielding in an outward direction when this corresponds to the concept of resiliency and the material of the spring. However, and in most instances, the U-shaped spring will act not unlike a clamp in such a way that its legs are pushed apart.

In accordance with a special modification of the U-shaped bendable spring, it is provided that the ends of the bendable spring cooperate with two slide surfaces which slope outwardly away from each other and that the bendable spring can be spread as a result of shifting along the slide surfaces by means of an actuating element which acts upon the U-shaped web.

In such instance, there is no need for rollers. The spring is not pushed aside by the first coupling member itself so that it would "snap" in or out. Since it is opened for the purpose of securing or releasing by the actuating element, its countersurface can lie at right angles to the undercut portion with reference to the direction of insertion or extraction of the anchor. An advantage of this modification is that it is not necessary to apply any separating force. On the other hand, the retaining force is large.

Finally, it is proposed in accordance with a further development of the invention to arrange three or more detent elements in such a way that the first coupling member is held exclusively by the detent elements. In this manner, one can exclude any friction between the first coupling member and the second coupling member. Wear is concentrated upon those parts which—see above—are preferably mounted to be exchangeable. It is also thinkable to resort to a combination of detent elements with rollers on shafts which are fixedly mounted on the second coupling member.

However, and as a rule, the hollow cross section of the second coupling member will conform, substantially without play, to the cross section of the first coupling member.

It will be appreciated that sufficient material should be left adjacent that recess of the second coupling member which conforms to the insert member in order to ensure that the second coupling member will exhibit the required stability. Several webs of material should remain in the region of the recess between the upper and lower parts of the second coupling member to establish a connection between such parts.

As a whole, the recess will assume the shape of a branched out system of slots. For an insert member in the form of a bendable spring, the height of the slot slightly exceeds the diameter of the spring except for the enlargements which serve for insertion into and for retention of a roller which should be free to turn without obstruction. If the insert member is in the form of a resilient holder, the height of the recess must equal the slightly greater height of such insert member.

The material which comes under consideration for the spring as well as for the holder, as well as the material for the rollers, can also be a plastic substance, for example, polyacetol. Such plastic material is characterized by minimal friction values vis-a-vis metals and also exhibits a pronounced stability and good spring characteristics. The utilization of plastic material is made possible because, and as explained hereinabove, the spring is inserted only subsequent to completion of the making of the parts of the prosthesis.

However, it is equally possible to employ metals which are customarily used in dental prostheses and include a range of metals from gold-platinum alloys to special steel, it being preferred to apply a coating of polytetrafluoroethylene in order to reduce friction.

BRIEF DESCRIPTION OF THE DRAWINGS

The invention will be explained in greater detail with reference to the embodiments which are shown in the drawing. There are shown in FIG. 1 a first coupling member with applied holding disc in a perspective view, FIG. 2 the first coupling member of FIG. 1 in a side elevational view, FIG. 3 a side elevational view of a modified first coupling member, FIG. 4 a section along the line IV—IV in FIG. 5 through a first coupling member and a second coupling member, FIG. 5 a section along the line V—V through the second coupling member of FIG. 4, FIG. 6 first coupling member and second coupling member of FIG. 4 in a side elevational view, FIG. 7 an occlusal partly sectional view of a detachable prosthesis which is attached to a fixed part of the prosthesis, FIG. 8 a fragmentary longitudinal sectional view along the line I—I of FIG. 9 through an anchor for dental prostheses which consists of a second coupling member and a first coupling member.

DESCRIPTION OF PREFERRED EMBODIMENTS

Figure 1:
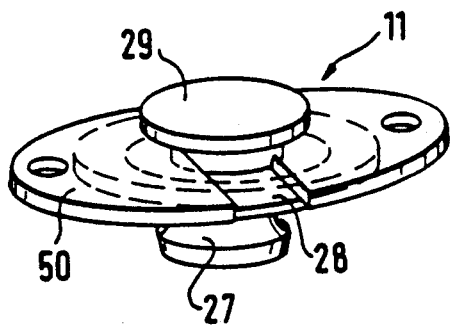
Figure 2:
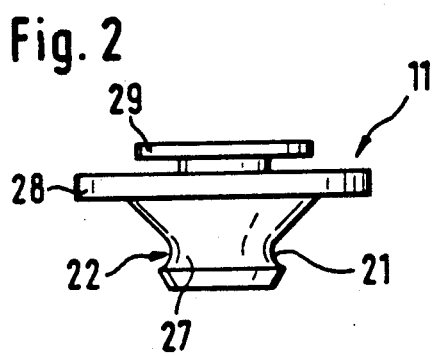

FIGS. 1 and 2 respectively show in a perspective and a side elevational view a first coupling member of a newly developed anchor for use in dental prostheses. The first coupling member 11 comprises a retaining element in the form of a lower part 27 with an undercut narrower portion 22 which is adjacent a separation ramp 21. The angle of the separation ramp 21, as well as the friction coefficient and the force of a spring to be described hereinafter determine the force which is required to separate the withdrawable part of the prosthesis from the fixedly mounted part of the denture.

The upper side of the first coupling member 11 comprises a disc-shaped supporting surface 28 and above the latter a retaining disc 29 into which can be pushed, for example, a holding disc 50 which enlarges the connecting surface.

Figure 3:
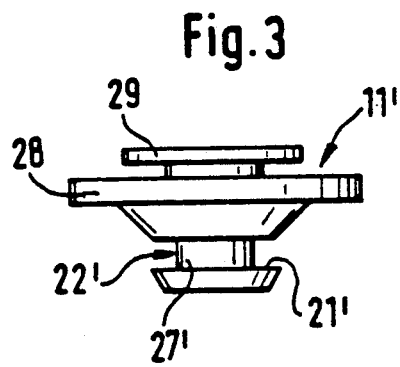

FIG. 3 shows a modifed first coupling member 11'. Its supporting surface 21' and the direction of separation or the symmetry axis of the first coupling member 11 make an angle of approximately 90 degrees. Such an anchor is self-locking; the connection between the first coupling member 11' and the associated second coupling member can be terminated only subsequent to disengagement of the spring which furnishes the retaining action. This will be described in greater detail with reference to FIG. 7.

Figure 4:
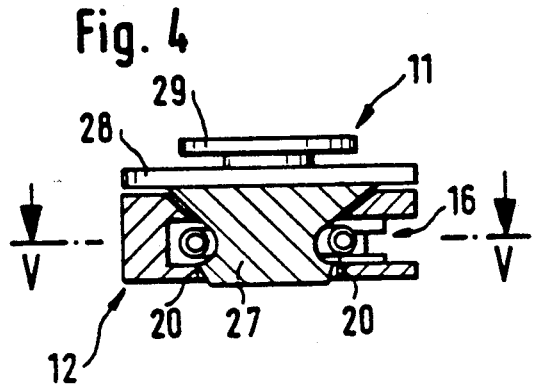
Figure 6:
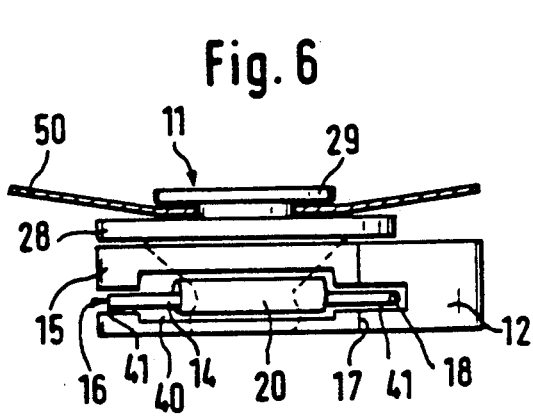
Figure 5:
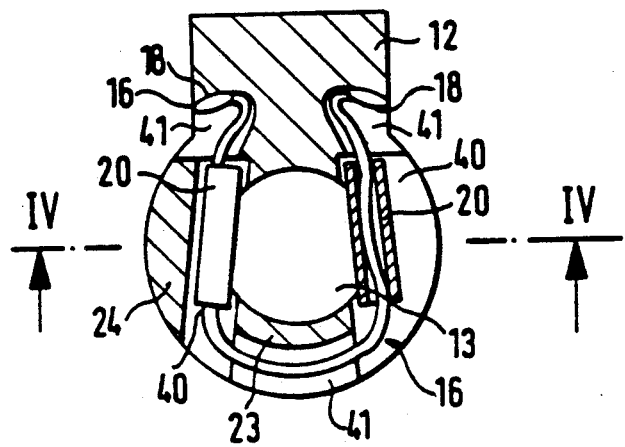

FIGS. 4, 5 and 6 show the construction of the second coupling member 12 which belongs to the first coupling member 11 of FIG. 2. Since the second coupling member 12 need not take up any chewing forces but only those forces which develop during insertion and removal of the prosthesis and can be defined with a high degree of accuracy due to the novel construction, the dimensions can be reduced to an absolute minimum. It is readily possible to achieve heights of less than 1 mm. The second coupling member 12 is provided with a flat slot 16 which starts at the front side 15, and there remain material webs 23, 24 in order to ensure the stability. A U-shaped spring 14 is inserted into the flat slot 16 from the front side. The ends 18 of the spring 14 lie resiliently in corresponding depressions of the slot 16 to be thus secured against falling out without interfering with the insertion and removal of the spring 14, for example, for the purposes of repair.

The ends 18 of the spring 14 are secured against lateral yielding due to appropriate configuration of the slot 16. In this manner, the legs 17 of the spring 14 can be spread apart in response to the application of force to the web of the spring as will be described in greater detail with reference to FIG. 7.

Rollers 20, here shown in the form of hollow cylinders, are rotatably slipped onto the legs 17 of the spring 14 in the region of a bore 13 which is provided in the second coupling member 12 and the shape of which conforms to that of the first coupling member 11.

These rollers 20 ensure that, during insertion and removal of the first coupling member 11, there develops only rolling friction which is minimal as is well known. This renders it possible to even more accurately define the detaching and retaining forces. In addition, the useful life is prolonged considerably due to greatly reduced wear as a result of rolling friction.

As can be seen particularly in FIG. 6, appropriate profiling of the slot 16 should ensure that the spring 14, which serves as a rotary shaft, is fixed in such a way that the rollers 20 are free to rotate in the slot.

To this end, the slot 16 has higher regions 40 for the rollers 20 and flatter regions 41 which are located at opposite sides of the rollers 20 and serve to axially hold the spring.

Figure 7:
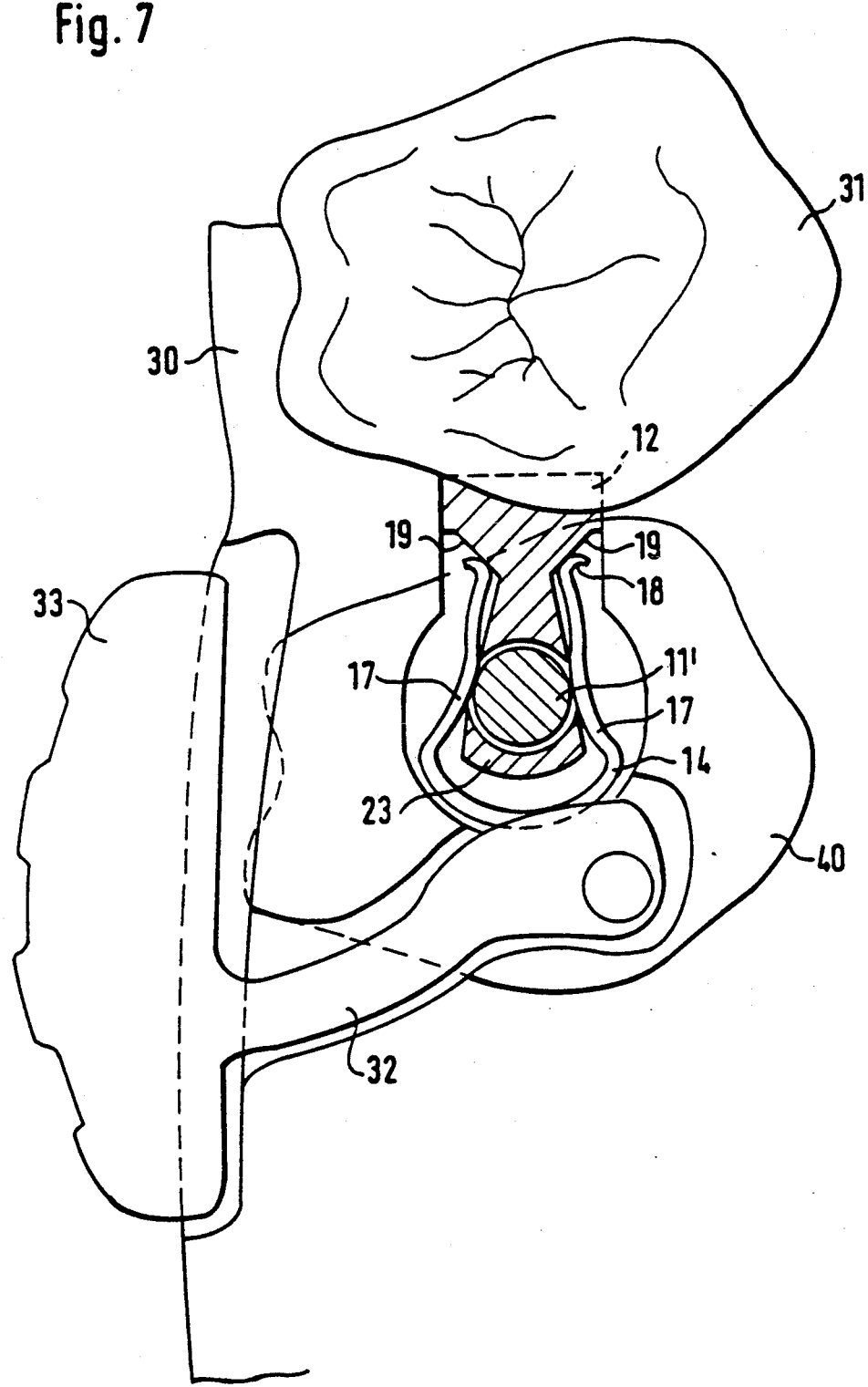

FIG. 7 shows an embodiment in which, first of all, the legs 17 of the spring 14 extend directly into the undercut narrower portion 22 of the first coupling member 11. However, spreading ramps 19 are provided in the slot 16 in the regions of the ends 18 of the spring 14. If the wearer of the prosthesis pivots the actuating lever 32,33 which is mounted in the removable part 30 of the denture, the lever 32 exerts pressure upon the base of the spring 14. The latter is displaced whereupon the ends 18 slide along the spreading ramps 19 and the legs 17 of the spring 14 are spread apart. When the spring 14 is in the spread-apart condition, the second coupling member 12 and the first coupling member 11 can be separated from each other in the absence of withdrawing forces. Owing to such construction, it is possible to employ here the self-locking first coupling member 11' which is shown in FIG. 3.

The first coupling member 11' is fixed, in a manner known per se, to a fixedly mounted part of the denture, for example, to a root cap 40. However, it is also possible to secure the second coupling member 12 to a crown 31 and to secure the first coupling member 11 to the removable part 30 of the prosthesis.

Figure 8:
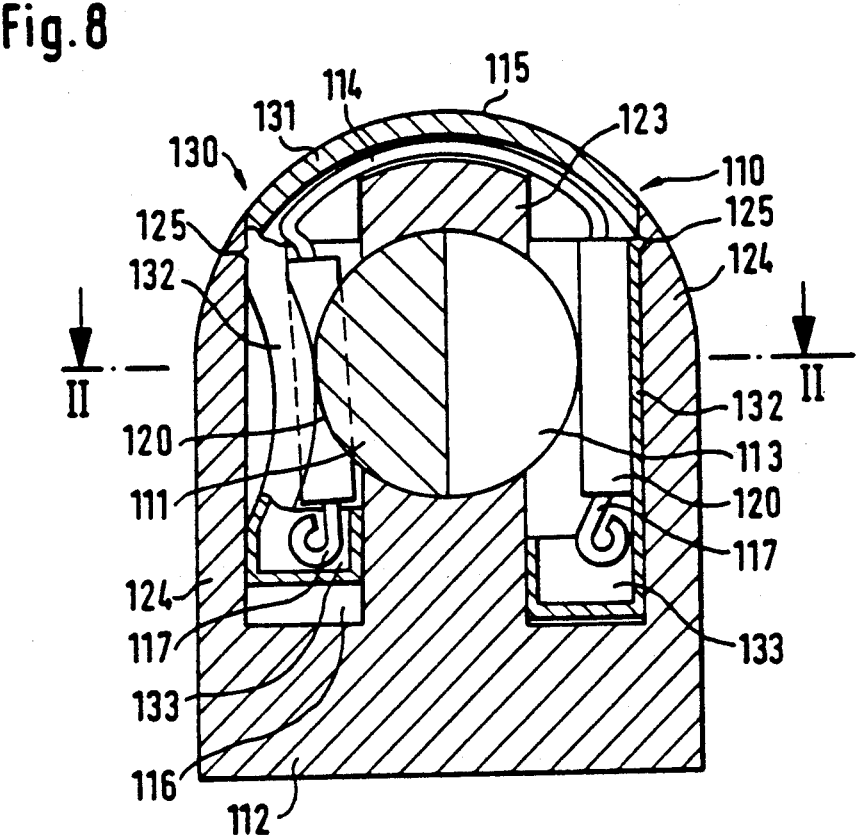
Figure 9:
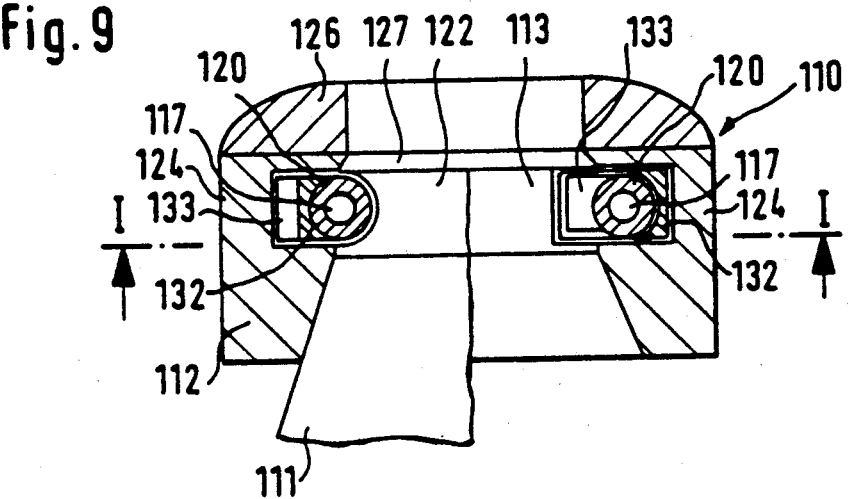
FIG. 9 is a fragmentary transverse sectional view of the anchor as seen from the line II—II in FIG. 8.

The first coupling member 111 of FIGS. 8 and 9 also comprises a holding element in the form of a lower portion 127 having an undercut narrower portion 122 the design of which has great bearing upon the holding and releasing forces between the first coupling member 111 and the second coupling member 112.

The associated second coupling member 112 is a flat metallic element with a central opening 113 the configuration of which conforms to that of the first coupling member 111. A flat slot 116 is machined into the second coupling member, starting at the front side 115; connecting webs 123, 124 take care of adequate stability of the second coupling member 112 and impart to the slot 116 a U-shaped configuration.

An insert element 130 is pushed into the slot 116 from the front side 115. The insert element has a U-shaped cross-sectional outline and is open in a direction toward the central bore 113. The insert element 130 consists of a springy metal or synthetic plastic material, for example, polyacetal. Its dimensions are selected in such a way that its U-shaped web 131 fills the slot 116 and clampingly fixes the insert element 130. On the other hand, the U-legs 132 are freely movable in the slot 116.

A steel wire 114, which is bent into the shape of a U, is inserted into the insert element 130 to serve as a shaft. Rollers 120, again in the form of sections of a cylindrical tube, are slipped onto and rotatably fixed on the legs 117 of the steel wire 114. These rollers enter the depression 122 of the first coupling member 111.

Alternatively, the U-shaped shaft 114 can be caused to pass through and to be secured in two openings of the insert element 130.

The U-legs 132 of the insert element 130 extend inwardly and abut the rollers 120. In this manner, they effectively assist the springy shaft 114 and thus prevent a breakage of the shaft 114. The free ends 133 of the insert element 130 are free to move longitudinally in the slot 116 and thus ensure the necessary longitudinal compensation during elastic deformation.

In the regions of the rollers 120, the legs 132 of the insert element 130 are provided with cutouts so that, at these locations, the full height of the slot 116 is available for the rollers 120. However, at both sides of the rollers, the legs 117 of the spring 114 are axially propped in narrower spaces of the insert element 130.

Here, again, the dimensions of the second coupling member 112 can be reduced to an absolute minimum, heights of less than 1 mm being readily achievable. The wear upon the rollers 120 on the one hand and upon the first coupling member 111 on the other hand is minimal so that it is possible to maintain predetermined holding- and releasing forces for long periods of use of the prosthesis. If necessary, the second coupling member 112 can be provided with a reinforcement 126.

I claim:

1. An anchor for securing a detachable part to a fixedly mounted part of a dental prosthesis, comprising a first coupling member which is provided with an undercut and a second coupling member which annularly surrounds the first coupling member and has at least one resilient detent element which extends into the undercut, the detent element extending through the undercut tangentially of the first coupling member and being held in a flat recess of the second coupling member at both sides of the location where the detent element extends into the undercut of the first coupling member to resiliently yield in the recess substantially radially of the first coupling member during insertion of the first coupling member into and during extraction of the first coupling member from the second coupling member.

2. Anchor according to claim 1, wherein said second coupling member has two detent elements which are disposed opposite each other.

3. Anchor according to claim 1, wherein the at least one detent element is provided on a U-shaped insert member which can be pushed into and withdrawn from a complementary recess of the second coupling member, the insert member being accommodated in a slot which is open toward the periphery of the second coupling member.

4. Anchor according to claim 3, wherein the undercut portion of the first coupling member has a slope extending at an angle such that the first coupling member can be extracted from the second coupling member with a predetermined force as a result of pushing back the at least one detent element.

5. An anchor for securing a detachable part to a fixedly mounted part of a dental prosthesis, comprising a first coupling member having an undercut, and a second coupling member which annularly surrounds the first coupling member and has at least one resilient detent element which extends into the undercut, the detent element extending substantially tangentially of the first coupling member and being held in a flat recess of the second coupling member at both sides of the location where the at least one detent element extends into the undercut of the first coupling member, the at least one detent element being provided on a substantially U-shaped insert member which can be pushed into and withdrawn from a complementary recess of the second coupling member, the insert member constituting a bendable spring and the at least one detent element consistituting a leg of the bendable spring, the leg being surrounded by a roller and the insert member having a web extending into a slot which is provided in and is open toward the periphery of the second coupling member.

6. Anchor according to claim 5, wherein the spring has two legs which are arched slightly inwardly.

7. Anchor according to claim 5, wherein the spring has two legs which are bent inwardly close to their ends in order to be anchored in the second coupling member and extend behind a narrowed portion which is provided in the second coupling member.

8. Anchor according to claim 5, wherein the spring has two ends which are held-against yielding in an outward direction.

9. Anchor according to claim 5, wherein the bendable spring has ends which cooperate with two slide surfaces of the second coupling member, the slide surfaces sloping outwardly away from each other and the bendable spring being spreadable as a result of shifting along the slide surfaces by means of an actuating element which acts upon a web of the spring.

10. Anchor according to claim 5, wherein the undercut potion of the first coupling member has a base and the roller has a cylindrical or concave circumference conforming to the base of the undercut portion of the first coupling member.

11. An anchor for securing a detachable part to a fixedly mounted part of a dental prosthesis, comprising a first coupling member having an undercut, a second coupling member which annularly surrounds said first coupling member and has at least one resilient detent element which extends into the undercut, the at least one resilient detent element extending substantially tangentially of the first coupling member and being held in a flat recess of the second coupling member at both sides of the location where the detent element extends into the undercut of the first coupling member, the at least one detent element being provided on a substantially U-shaped insert member which can be pushed into and withdrawn from a complementary recess of the second coupling member, the insert member having a web extending into a slot which is provided in and is open toward the periphery of the second coupling member and the insert member constituting a resilient retainer for the at least one detent element and the at least one detent element comprising a roller mounted on a shaft.

12. Anchor according to claim 11, wherein the substantially U-shaped insert member has an inwardly open U-shaped cross section.

13. Anchor according to claim 11, wherein the shaft for the roller is formed by a leg of a U-shaped bendable spring.

* * * * *